(12) United States Patent
Shlyonsky et al.

(10) Patent No.: US 11,794,088 B2
(45) Date of Patent: Oct. 24, 2023

(54) METHODS AND SYSTEMS FOR SWIM ANALYSIS

(71) Applicant: MYSWIMEDGE INC., Houston, TX (US)

(72) Inventors: Igor Shlyonsky, Moscow (RU); Andy Stamm, Goch (DE); Riccardo Barbieri, Bologna (IT); Massimo Guarino, Bologna (IT)

( * ) Notice: Subject to any disclaimer, the term of this patent is extended or adjusted under 35 U.S.C. 154(b) by 99 days.

(21) Appl. No.: 17/518,730

(22) Filed: Nov. 4, 2021

(65) Prior Publication Data
US 2022/0241672 A1 Aug. 4, 2022

Related U.S. Application Data

(60) Provisional application No. 63/145,669, filed on Feb. 4, 2021.

(51) Int. Cl.
*A63B 24/00* (2006.01)
*A63B 71/06* (2006.01)
*A63B 69/12* (2006.01)

(52) U.S. Cl.
CPC ...... *A63B 71/0686* (2013.01); *A63B 24/0003* (2013.01); *A63B 69/12* (2013.01); *A63B 71/0622* (2013.01); *A63B 2071/0655* (2013.01); *A63B 2071/0663* (2013.01); *A63B 2071/0694* (2013.01); *A63B 2208/03* (2013.01); *A63B 2220/30* (2013.01); *A63B 2220/40* (2013.01); *A63B 2220/62* (2013.01); *A63B 2220/836* (2013.01); *A63B 2225/20* (2013.01); *A63B 2225/74* (2020.08)

(58) Field of Classification Search
CPC . A63B 71/0686; A63B 24/0003; A63B 69/12; A63B 71/0622; A63B 2225/74; A63B 2071/0655; A63B 2071/0663; A63B 2071/0694; A63B 2208/03; A63B 2220/30; A63B 2220/40; A63B 2220/62; A63B 2220/836; A63B 2225/20
See application file for complete search history.

(56) References Cited

U.S. PATENT DOCUMENTS

2018/0369637 A1* 12/2018 Hoang ................ G09B 19/003

* cited by examiner

*Primary Examiner* — Robert P Bullington, Esq.
(74) *Attorney, Agent, or Firm* — Nadya Reingand

(57) ABSTRACT

Automatic swimming analysis and nearly immediate feedback on a user device is disclosed. A sensor placed on a swimmer's waistline instantaneously measures data of the swim, allows to upload this data to a cloud system performing immediate analysis using algorithms. The cloud system provides feedback which helps determine proper (or improper) swimming techniques, comparing patterns to own past swims or to professional swimmers. The sensor enables stroke improvement with output including graphs, single numerical values, and detailed single-stroke data. The output provides both easy to understand metrics for amateur swimmers as well as more technical analysis options for advanced users. Metrics for amateurs can include swim symmetry analysis, speed consistency analysis, and stroke consistency analysis. More technical/detailed information includes comparison of strokes of each arm to the other, comparison of strokes made by left and right arms, mathematical analyses of strokes, and average, maximum, minimum, and instantaneous speeds.

20 Claims, 8 Drawing Sheets

TOP DOWN VIEW    THREE QUARTER VIEW    SIDE VIEW
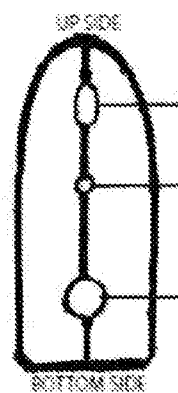  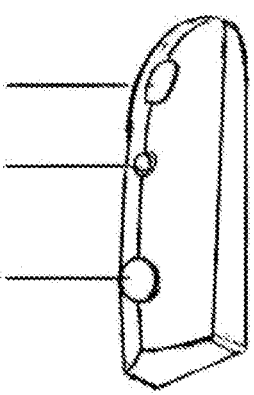  
FIG. 1A            FIG. 1B              FIG. 1C
BOTTOM VIEW
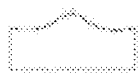
FIG. 1D
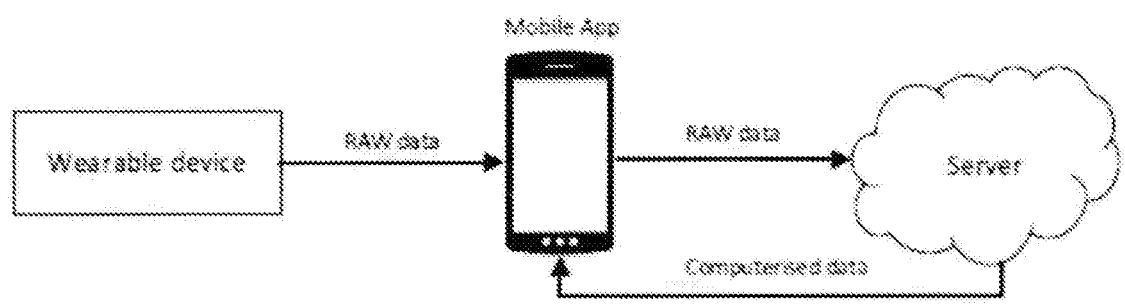
FIG. 2

INDIVIDUAL STROKE ANALYSIS

| PARAMETER | Average velocity, m/s | Min velocity, m/s | Max velocity, m/s | Average stroke time, sec | Stroke rate |
|---|---|---|---|---|---|
| Right arm | 1.517 | 1.013 | 1.910 | 1.229 | |
| Left arm | 1.047 | 0.827 | 1.353 | 1.189 | 24.81 |
| Right arm | 1.008 | 0.826 | 1.240 | 1.279 | |
| Left arm | 1.053 | 0.830 | 1.397 | 1.229 | 23.92 |
| Right arm | 1.018 | 0.833 | 1.197 | 1.337 | |
| Left arm | 1.067 | 0.919 | 1.284 | 1.102 | 24.60 |
| Right arm | 1.034 | 0.899 | 1.243 | 1.277 | |
| Left arm | 1.075 | 0.867 | 1.383 | 1.210 | 24.13 |
| Right arm | 1.035 | 0.902 | 1.237 | 1.308 | |
| Left arm | 1.093 | 0.951 | 1.331 | 1.081 | 25.12 |

FIG. 4

KEY METRICS

| Symmetry score<br>Based on the distance covered by strokes of left and right arms | Left arm | Right arm |
|---|---|---|
| | 50% | 50% |
| Speed stability score<br>The lower the number the more stable is the speed of swim | 51.8% | |
| "Best stroke based" lap time<br>Based on the lap's best stroke | 28.23 | |

FIG. 5

INDIVIDUAL STROKE ANALYSIS
| PARAMETER | Average velocity, m/s | Min velocity, m/s | Max velocity, m/s | Average stroke time, sec | Stroke rate |
|---|---|---|---|---|---|
| Right arm | 1.828 | 0.607 | 2.098 | 0.540 | |
| Left arm | 1.549 | 1.450 | 1.607 | 0.711 | 48.35 |
| Right arm | 1.522 | 1.309 | 1.899 | 0.680 | |
| Left arm | 1.507 | 1.344 | 1.682 | 0.550 | 47.78 |
| Right arm | 1.537 | 1.351 | 1.721 | 0.671 | |
| Left arm | 1.526 | 1.402 | 1.676 | 0.570 | 48.35 |
| Right arm | 1.568 | 1.357 | 1.787 | 0.701 | |
| Right arm | 1.523 | 1.358 | 1.762 | 0.551 | 47.92 |
FIG. 6
STROKE LENGTH GRAPH ALL LEFT ARM STROKES STROKE LENGTH GRAPH ALL RIGHT ARM STROKES
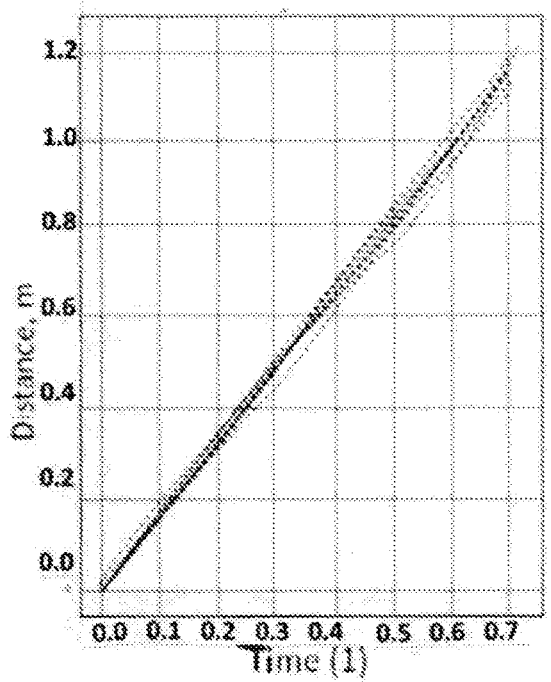
FIG. 7A
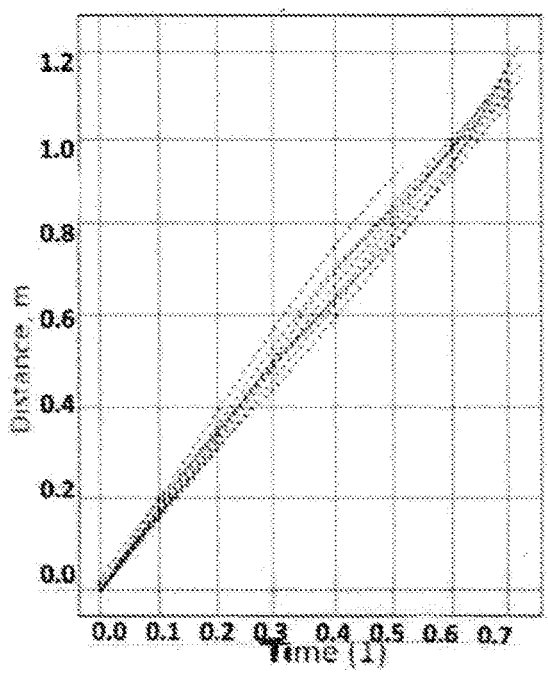
FIG. 7B

LAP INDICATORS

| Parameter | Number | Variations |
|---|---|---|
| Total lap time, sec | 31.23 | |
| Glide timing, sec | 0.63 | |
| Swimming timing, sec | 30.66 | |
| Mean velocity over a lap, m/sec | 1.603 | +/- 31.18% |
| Average stroke rates over a lap | 48.07 | +/- 2.80% |

FIG. 8A

KEY METRICS

| | Left arm | Right arm |
|---|---|---|
| Symmetry score<br>Based on the distance covered by strokes of left and right arms | 45% | 55% |
| Speed stability score<br>The lower the number the more stable is the speed of swim | 25.2% | |
| "Best stroke based" lap time<br>Based on the lap's best stroke | 28.89 | |

FIG. 8B

METHODS AND SYSTEMS FOR SWIM ANALYSIS

CROSS-REFERENCE TO RELATED APPLICATIONS

The present patent application is a non-provisional application, claiming priority to Provisional U.S. Patent Application Ser. No. 63/145,669, filed Feb. 4, 2022, said application and its disclosures being incorporated herein by reference in its entirety.

FIELD OF THE INVENTION

This invention relates to the field of devices, methods, and systems for swim training and swim technique analysis.

BACKGROUND ART

Sensors in sports are nowadays widely used. Inertial Measurement Units (IMUs) including but not limited to accelerometers (Micro Electro-Mechanical Systems—MEMS) tend to be used more often in sports monitoring. In swimming, these sensors have seen rapid development in the past years. These sensors have very good measurement capabilities today, but the automatic analysis of the gathered data has yet to be implemented optimally. The present invention addresses such issues with the prior art, as discussed hereinbelow.

SUMMARY OF THE INVENTION

The present invention provides an automatic swimming analysis and nearly immediate feedback on, e.g., a smartphone/tablet. The methodology of the invention is implemented for swimmers ranging from novice to elite.

A sensor that is placed on a swimmer's waistline, particularly the sacrum, and instantaneously measures detailed data of a freestyle swim provides data to algorithms which detect and determine a correct or incorrect swimming technique via patterns, enabling a user to improve based on one or more graphs and/or single numerical values output by the inventive method/system.

Data analysis enables swimming analysis on different levels: easy to understand metrics for amateur swimmers, and more technical analysis for the professional swimmers and coaches. Metrics for amateurs can include swim symmetry analysis, speed consistence analysis, and stroke consistency analysis. More technical information includes comparison of strokes of each arm to the other, comparison of strokes made by left and right arms, mathematical analysis of strokes, and average, maximum, minimum, and instantaneous speeds.

Metrics produced by the invention include indices, which can be different depending on the skill level of the swimmer and his/her ability to provide the strokes needed to create sufficient index data. The Symmetry Index can rely on the distance alone, or it can take into account distance, time, and speed, as well as variation of the strokes to provide more complex analysis.

Algorithms allow to automatically determine key areas for swimming technique improvement.

Algorithms allow for comparing swimming technique of the same swimmer at different speed and skill levels.

Algorithms allow for comparing swimming techniques of different swimmers.

Algorithms allow for amateur swimmers to develop their technique based on the swimming technique of elite swimmers. Development may be performed at different speed levels and may be based on various anthropomorphic parameters.

Algorithms allow for testing hypotheses on swimming technique improvement as well as root cause analysis. Such hypotheses include but are not limited to changes in body positioning, kick/leg parameters, head positioning, inhaling, etc.).

The methodology also includes specific exercises to improve particular areas of a swimming technique or a swimmer body.

The methodology further allows for checking swim technique improvements on the micro level—i.e., the level of each individual stroke, rather than on the macro level (e.g., mean lap velocity, average stroke rate, number of strokes, etc.).

The methodology allows for combining the analysis of sensor data with a video analysis of a full swim and/or individual strokes of the swimmer.

The approach allows for the testing of various elements while swimming with different techniques.

BRIEF DESCRIPTION OF THE DRAWINGS

The present invention will now be discussed in further detail below with reference to the accompanying figures in which:

FIGS. 1A-1D show an embodiment of the device (i.e., sensor) placed on the user's waistline, e.g., at the sacrum. FIG. 1A shows a top view, FIG. 1B shows a perspective (i.e., three-quarter) view, FIG. 1C shows a side view, and FIG. 1D shows a bottom view.

FIG. 2 shows key components of the inventive system, the relations between the key components, and the information flow between the key components.

FIG. 4 shows an example of detailed information automatically provided through the inventive method/system, comprising information about individual left and right swim strokes from a given lap.

FIG. 5 shows an exemplary table automatically produced by the inventive method/system with simple, i.e., high-level, information about a lap, comprising the symmetry score, speed stability score, and best stroke-based lap time.

FIG. 6 shows an individual stroke analysis table provided via the method/system. The right-most column exemplifies the inconsistent stroke rates of a less advanced swimmer during a 25-meter swim.

FIGS. 7A-7B and 7C-7D show a comparison of a swimmer's left and right arm strokes, as provided by the present invention. FIG. 7A shows a comparison of stroke lengths for left arm strokes, while FIG. 7B shows a comparison of stroke lengths for right arm strokes.

FIG. 7C shows a comparison of stroke speeds for left arm strokes, and FIG. 7D shows a comparison of stroke speeds for right arm strokes.

FIG. 8A-8C shows an example report based on cloud-based system output provided to a swimmer nearly immediately (e.g., within 2 minutes) after swim data is collected via the wearable sensor and transmitted from the sensing device to the cloud system.

DETAILED DESCRIPTION OF THE PREFERRED EMBODIMENTS

Figure 3A:
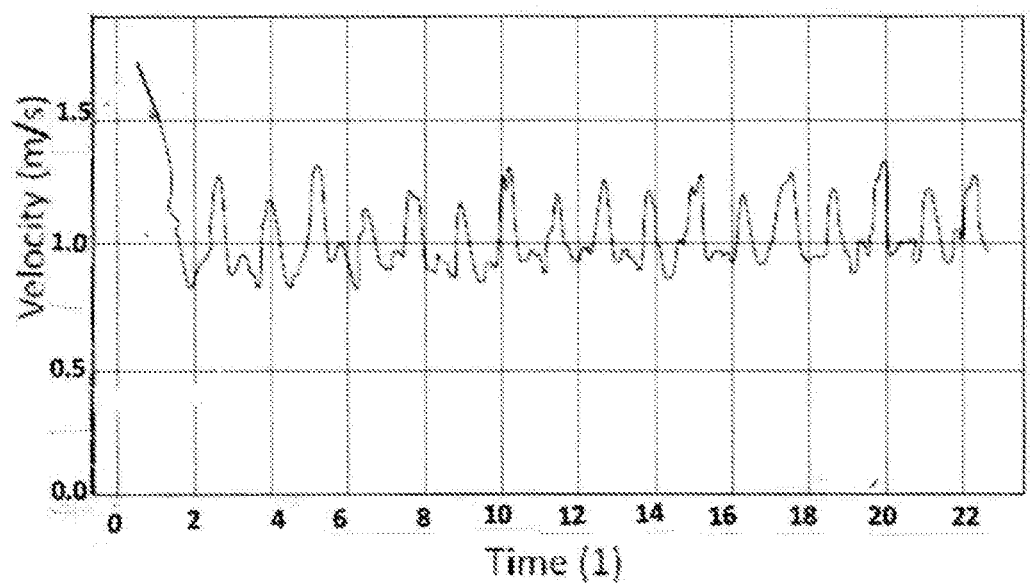
FIGS. 3A-3B show exemplary graphs automatically produced by the inventive method/system, showing the changes in velocity of a first swimmer (FIG. 3A) and a second swimmer (FIG. 3B) over time.
Figure 3B:
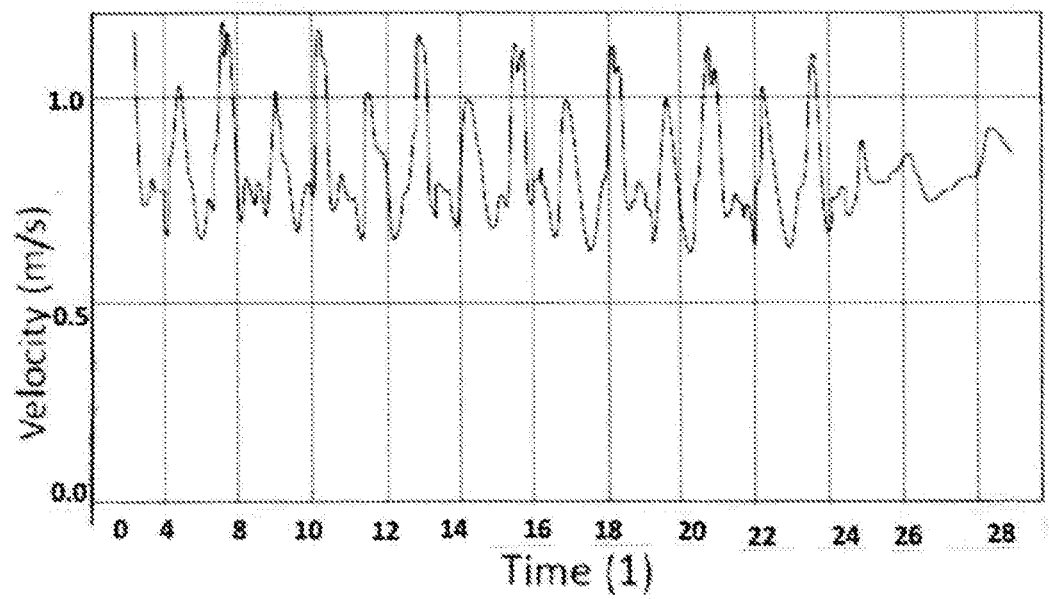

In the following description, for purposes of explanation, specific examples are set forth to provide a thorough understanding of the present invention. However, it will be apparent to one skilled in the art that these specific details are not required in order to practice the present invention. The same techniques can easily be applied to other types of similar systems.

A single sensor that is placed on the swimmer's sacrum can measure a lot of details of the swim that would allow the algorithms to detect and determine correct or incorrect swimming technique patterns and enables a swimmer and her/his coach to work on their improvement.

The sensor has a 3-axis accelerometer, -magnetometer, -gyroscope, rechargeable battery, internal memory, two control buttons, a vibration mechanism, and a multi-color LED light. A sole sensor is all that is required for measurement and analysis, each sensor having dimensions of about 70 mm×35 mm×13 mm.

The device can operate in several states: off, Bluetooth Low Energy (BLE) advertising, BLE connected, sample mode ready, and sample mode active. The sensor also can be reset.

The two control buttons are located on the outer side of the sensor (i.e., that side of the sensor facing away from the swimmer), such that they can be pressed when the sensor is positioned on the back of an active swimmer. The state of the sensor can be monitored either through the LED light or through the vibration mechanism, making it convenient for a swimmer to control the functioning of the sensor.

Two buttons are programmed in a way to switch from mode to mode depending on whether it is short press or long press and also depending on the current state of the sensor.

Once turned on the sensor automatically pairs with a smartphone that it was paired with before.

After the swim, with the pressing of one button, the swim data is transmitted to the server, and from the server, the results of the analysis are transferred to the application, where the swimmer or coach is able to review, analyze, and act on such information.

The developed and utilized inventive algorithms allow for the tracking of changes in acceleration and speed during each stroke, and whether the stroke was made by the right or left hand. Information about each stroke is stored on the server which enables analysis of the swimming technique on various levels: e.g., in-depth stroke analysis, consistency of strokes analysis, comparison of left and right arm, analysis of technique at different speeds and skill levels.

The acceleration data recorded by the IMU is initially converted to gravitational units before it is high pass filtered to separate the sensor orientation from the desired acceleration signal. This filter is applied to remove, e.g., the gravity signal from the acceleration signal. A zero-crossing algorithm is further applied to the data to automatically separate the left and right arm strokes.

Then the information on the changes in acceleration and speed during each stroke and lap is processed to generate data on each swim.

The information that the algorithms calculate include but are not limited to: maximum, minimum, and average speed of each stroke, variations in maximum, minimum, and average stroke speeds, or separately by strokes of right or left arms, distance per stroke for each individual stroke, each individual stroke rate, and average acceleration during each stroke. The method also builds graphs for each lap: e.g., graph of speed and acceleration changes during each lap, graph of speed changes of right (or left) arm strokes only, graph of distance covered by each stroke, etc.

Captured sensor data analysis allows for swimming technique analysis on various levels: the method/system can create easy to understand metrics, e.g., for amateur swimmers, or more technical analysis, e.g., for the professional swimmer and/or coach. Simple metrics can include, e.g., swim symmetry analysis, speed consistency analysis, and stroke consistency analysis. More technical information includes, e.g., comparison of strokes of each arm to the same arm, different stroke, comparison of strokes made by left vs. right arms, mathematical analysis of strokes, and average, maximum, and minimum speeds per stroke.

Turning now to FIG. 5, the symmetry index (i.e., symmetry score), as it is shown in the table, demonstrates what proportion of the total distance is swum using either the right or the left arm. In the case that there is a strong user tendency to utilize one arm over another, a swimmer or coach might decide first whether this is something that they would like to correct, or if it is a part of a desired technique, the symmetry index is able to provide a relational score to be analyzed by the user.

The speed stability score provides information on the uniformness of swim speed over time. A lower speed stability score shows greater uniformity in speed, e.g., that the swimmer is trying to preserve an average speed, whereas a high speed stability score shows less uniformity, e.g., that the swimmer is accelerating/decelerating more often than attempting an endurance workout, i.e., maintaining a speed. The speed stability score is thus a very useful manner of quantitatively determining key and differentiating swimming technique features based on how well speed is maintained and the particular goals of the swimmer. The speed stability score further allows for comparisons of the score with other swimmers and other laps of the same swimmer.

The "best stroke based" lap time calculates for the swimmer the potential lap time if every stroke was based on the swimmer's best stroke(s). This feature allows the swimmer/coach to identify what factors made these strokes the best strokes, thereby attempting to repeat these factors throughout future laps.

Key Metrics Provided by the Inventive Method/System.

Key metrics provided by the invention comprise single value scores which are generally based on relative indices, but which further provide quantitative information to the swimmer/user (these terms are used interchangeably throughout this description). This quantitative information provides a range of benefits to a user depending on their skill level and ability to utilize the single value score. The key metric calculations provided by the method/system may rely on a single factor, e.g., distance, or the calculations might take into account any combination of distance, time, speed, and other stroke data to provide a more complex analysis of swimming technique.

The key metrics provided by the method/system allow for a simpler way of understanding data, via the output of a single value from a plurality of sensor data (e.g., even a metric based on a single factor will be calculated from data comprising a plurality of values for that single factor, e.g., distance swum per stroke). The single value thereby immediately translates to a swimmer a key performance metric previously unavailable for training purposes, based on algorithms connecting key parameters of a swim into one output value. To provide an example of such calculation, the symmetry score between the right and left arms for a freestyle swim may be calculated based on a distance covered, a timing of each stroke, a swim speed, a swim acceleration, or any combination thereof. An exemplary calculation of symmetry score, based on distance, may be calculated as exemplified below.

Symmetry Score, based on a time (i.e., length of time) associated with each swim stroke:

Symmetry score left arm time=$SS_{lt}$ $$SS_{lt} = \frac{\text{left\_arm\_mean\_time}}{(\text{left\_arm\_mean\_time} + \text{right\_arm\_mean\_time})}$$

Symmetry score right arm time=$SS_{rt}$ $$SS_{rt} = \frac{\text{right\_arm\_mean\_time}}{(\text{right\_arm\_mean\_time} + \text{left\_arm\_mean\_time})}$$

This symmetry score provides a value over 50% i.e. for the left arm, if the time the left arm uses for a stroke is longer compared to the time taken with the right arm and vice versa for the right arm.

A second example of Symmetry Score calculation, based on distance, is provided below.

Symmetry Score, based on a distance associated with each swim stroke:

Symmetry score left arm distance=$SS_{ld}$ $$SS_{ld} = \frac{\text{left\_arm\_mean\_distance}}{(\text{left\_arm\_mean\_distance} + \text{right\_arm\_mean\_distance})}$$

Symmetry score right arm distance=$SS_{rd}$ $$SS_{rd} = \frac{\text{right\_arm\_mean\_distance}}{(\text{right\_arm\_mean\_distance} + \text{left\_arm\_mean\_distance})}$$

This symmetry score provides a value over 50% i.e. for the left arm, if the distance the left arm swum is longer compared to the distance swum with the right arm, and vice versa for the right arm.

It is noted that, similar to the above examples, additional symmetry scores may also be calculated and provided to the swimmer/coach, e.g., by time associated with more than a single stroke, by distances associated with more than a single stroke, by stroke speed, both individual and pluralities thereof, and by comparisons of graphical data created for each stroke.

In addition to the symmetries provided by the present invention, Stroke Stability Scores are also provided. Example calculations for the Stroke Stability Score, as calculated by the present method, are provided below.

Stroke Stability Score, left: =$SSS_l$ $$SSS_l = \left[ \frac{(\text{max\_mean\_velocity\_left} - \text{min\_mean\_velocity\_left})}{\text{mean\_velocity\_left}} * 100 \right]$$

Stroke Stability Score, right: =$SSS_r$ $$SSS_r = \left[ \frac{(\text{max\_mean\_velocity\_right} - \text{min\_mean\_velocity\_right})}{\text{mean\_velocity\_right}} * 100 \right]$$

Stroke Stability Score:

$$SSS = \frac{SSS_l + SSS_r}{2}$$

The Stroke Stability Score shows a number of 0 if the variation between minimum and maximum velocity (within the strokes) is equal zero. It gives the result of 100 if the variation between minimum and maximum velocity (within the strokes) is equal to the mean velocity. It provides a result of larger 100 if the variation between minimum and maximum velocity (within the strokes) is larger than the mean velocity. That means this score should be preferably in the lower order, perfectly (theoretical) at 0. In practice we have seen numbers <30 for professional international swimmers.

Thirdly, the present invention may also provide a best stroke-based lap time. The following exemplifies a calculation for best stroke-based lap time, as implemented by the present invention.

Best stroke lap time=$BS_{lt}$ $$BS_{lt} = (\text{total}_{lap_{time}} - \text{total}_{swim_{time}}) + \text{number\_left\_arm\_strokes} * \text{fastest\_left\_arm\_time} + \text{number\_right\_arm\_strokes} * \text{fastest\_right\_arm\_stroke}$$

The added benefits provided to the swimmer/user by the present invention through the Symmetry Scores, Stroke Stability Scores, and best stroke-based lap times are valuable to users, providing significantly more than a plurality of values that may be calculated via a more simplistic computer system. These added benefits are described hereinbelow.

The Symmetry Score (SS), based on various parameters as discussed above, provides the user with a significant amount of information on the technique, and the changes within the technique at different speeds and between left and right sides. The symmetry score (SS) provides the user a relative value quantifying the similarities in a right arm stroke versus a left arm stroke, and comprising a single numerical value obtained from a set of swim data collected by the wearable sensor. It is also notable that the Symmetry Score between left and right arms can be calculated based on a number of parameters, including average acceleration, speed, timing of each stroke, length of each stroke, and combinations thereof.

The Symmetry Score may also be used to determine the total length that the swimmer swam using either his/her left or his/her right arm. The methodology thereby also gives the swimmers and their coaches sufficient data to perform a deeper analysis of the arm symmetry.

The same approach can be applied to the Stroke Stability Score (SSS). The Stroke Stability Score may be calculated based on the maximum, the minimum, and/or the average speed for each arm. The methodology provides varying data in order to calculate the SSS in different ways. One manner compares the stability of all maximums, minimums, or average speeds of each stroke. It is also possible to compare the Stroke Stability Score for each arm separately. Additionally, swim data may be compared to digitized swim data located in a digitized library stored, e.g, on the cloud-based system performing the calculations. SS and SSS may thus be compared, alongside other stroke data, if desired. The comparisons may be of laps of the same swimmer, laps of different swimmers, and laps associated with digitized data stored on the cloud (e.g., advanced swim stroke data for various swimming styles and techniques).

Regarding the "Best Stroke-based" lap time, the data collected by the sensor provides the algorithms with sufficient information to calculate varying potential lap times using not only the best stroke, but also with an averaging of several high quality strokes, by removing from the calculation the worst strokes, etc.

Overall, the key metrics are calculated to create single value indications on how to improve swim technique which are beneficial to even the most novice swimmers. The key metrics are delivered to the swimmer in real-time, as soon as the data is received by the platform. It is also possible to enhance the calculations with additional sensor data to look at various facets of a swim for advanced swimmers and/or for swimming coaches. The algorithms thus allow for automatically determining key areas for various swimming technique improvements.

With the digitization of many parameters of the swimming the algorithm is set up to determine key areas for improvement. From the symmetry index and other basic metrics, the system/method can recommend exercises for improving stroke symmetry and speed stability. The method/system can also recommend other methods for checking/testing the swimmer's stroke symmetry and speed stability. Such recommendations include, e.g., swimming with an equal number of left arm strokes and right arm strokes, swimming at different speeds, swimming with a focus on maintaining a speed, or modifying individual strokes to test changes in technique results.

The method/system is also able to calculate the consistency of maximum and minimum speeds for each stroke, as well as the variability in timing for each stroke. A given user's exercises might be focused, e.g., on achieving more consistency in maximum or minimum speeds, or on minimizing the difference between minimum and maximum speed. The speed stability score (SSS) provided via the method/system allows for the swimmer following such a focus to instantaneously understand the results of a plurality of stroke data via a single numerical value output via the SSS.

The normalized stroke rate (NSR) is another singular numerical value output by the method/system which provides a relative value relating to any changes in stroke rate during a swim. More advanced swimmers will have a more consistent stroke rate over a lap, or perhaps the stroke rate increases during a lap. Amateur swimmers will have very inconsistent stroke rates. User exercises can be dedicated to swimming with a consistent stroke rate, or with a slightly increasing stroke rate, or even with the stroke rate increasing significantly over a lap. The SR, and automatic comparison of SRs, allows for the user to understand where in each lap they are lacking or overexerting.

Additional calculations may be performed by the user for a deeper analysis of the technique. Such additional calculations would utilize either the graphs provided via the system/method or the single numerical values provided via the SS, the SSS, or the "best stroke based" lap time, and might include, e.g., the timing of accelerations or decelerations during each stroke, an analysis of breathing parameters per stroke, a calculation of the interdependency of stroke timing, speed, and length, etc.

Figure 7C:
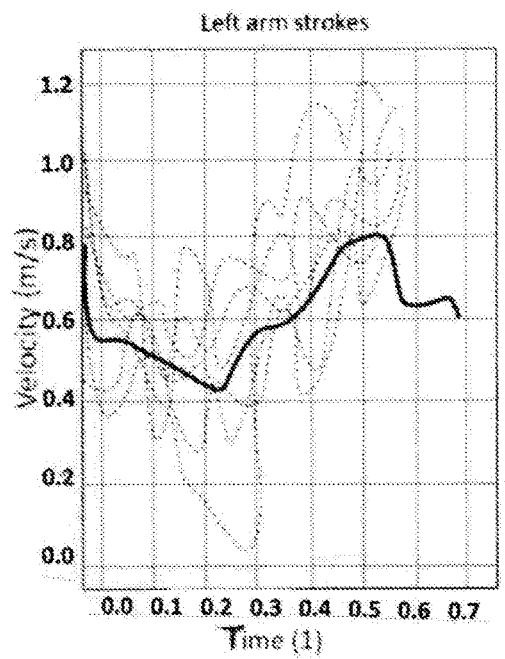
Figure 7D:
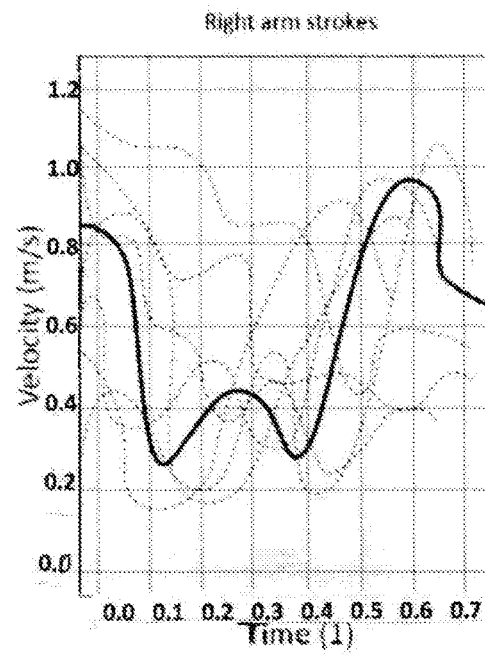
Figure 8C:
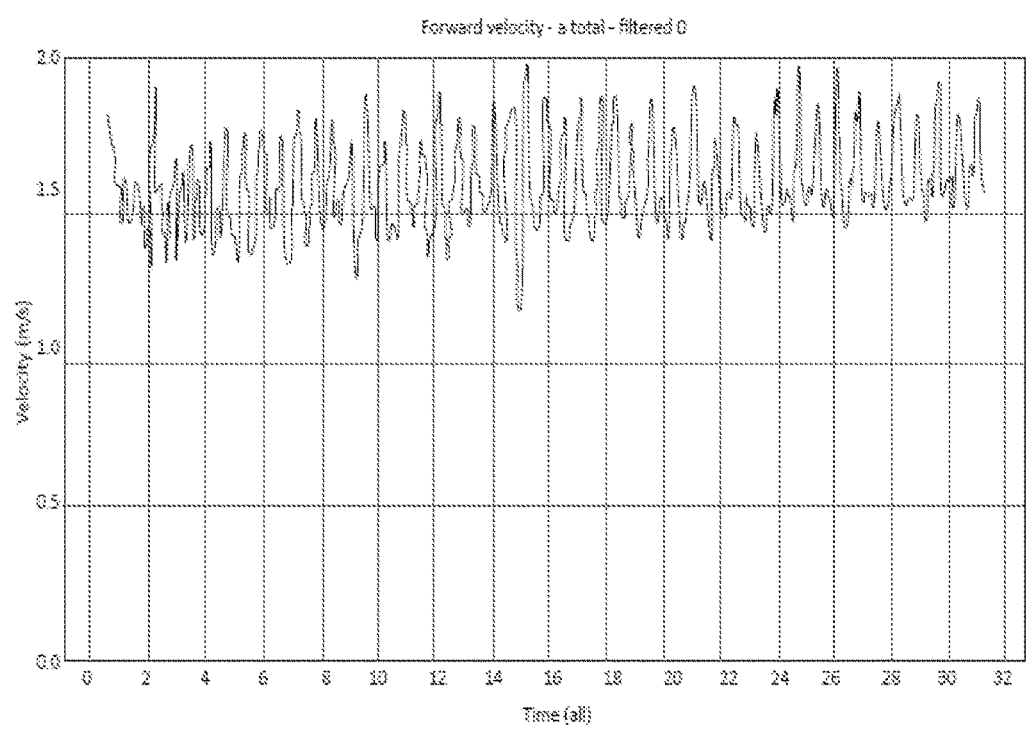

For example, as FIG. 7A-7D shows on the right side, a user may analyze a graphical representation of overlapping strokes. The graph may split right arm strokes and left arm strokes, as shown in the embodiment displayed in the figure, if desired by the user. Other graphical representations may show an overlap of all arm strokes, both left and right, within a given lap.

Within the scope of the invention is firmware, hardware, software and computer readable-media including software which is used for carrying out and/or guiding the methodologies described herein. Hardware optionally includes a computer, the computer optionally comprising a processor, memory, storage space and software loaded thereon. The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. When used in the following claims, the terms "comprises", "includes", "have" and their conjugates mean "including but not limited to". The scope of the invention is limited only by the following claims.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

The words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What is claimed is:

1. A method for analyzing a user's swim stroke, comprising:

recording swim data via a wearable sensor, said wearable sensor comprising a battery, a memory, a 3-axis accelerometer, a 3-axis gyroscope, and a 3-axis magnetometer, said wearable sensor thereby having 9 degrees of freedom, said wearable sensor being positioned solely on a user's sacrum during a swim, transmitting said swim data to a cloud-based system, said cloud-based system processing said swim data, said cloud-based system outputting a stroke symmetry score and a stroke stability score based on said processing, said stroke symmetry score providing a first value indicating any differential between a right arm stroke and a left arm stroke, said stroke stability score providing a second value indicating any differential between stroke velocities.

2. The method of claim 1, said cloud-based system further providing table data comprising the following for each individual arm stroke:
arm timing, maximum and minimum speed, stroke rate, and stroke variations.

3. The method of claim 1, said cloud-based system further outputting a best stroke-based lap time.

4. The method of claim 1, said cloud-based system further outputting a normalized stroke rate.

5. The method of claim 1, said cloud-based system further outputting a graphical representation of overlapping strokes.

6. The method of claim 5, the graphical representation comprising two parts, a first part showing right arm strokes, and a second part showing left arm strokes.

7. The method of claim 1, said cloud-based system further outputting a graphical representation of a normalized swimming velocity over a given distance.

8. The method of claim 1, said cloud-based system output being displayed on a mobile device.

9. The method of claim 1, said cloud-based system output being displayed on a user's watch.

10. The method of claim 1, said cloud-based system output being provided to the user within 2 minutes of the cloud-based system receiving said swim sensor data.

11. The method of claim 1, said cloud-based system output being provided to the user while the user remains in water.

12. The method of claim 1, wherein the wearable sensor records the swim data 100 times per second.

13. The method of claim 1, wherein the wearable sensor has dimensions of 70 mm×35 mm×13 mm.

14. The method of claim 1, wherein the stroke symmetry score is calculated based on a distance associated with each stroke.

15. The method of claim 1, wherein the stroke symmetry score is calculated based on a time associated with each stroke.

16. The method of claim 1, wherein the stroke symmetry score is calculated based on a speed associated with each stroke.

17. The method of claim 1, wherein the stroke symmetry score is calculated based on a value associated with multiple swim strokes.

18. The method of claim 1, wherein the cloud-based system output compares a first lap to a second lap of the same swimmer.

19. The method of claim 1, wherein the cloud-based system output compares a first swimmer to a second swimmer.

20. The method of claim 19, where data for the first swimmer is the swim data and wherein data for the second swimmer is chosen from a library of digitized swim data.

* * * * *